(12) United States Patent
Itamochi

(10) Patent No.: US 12,364,435 B2
(45) Date of Patent: Jul. 22, 2025

(54) MEDICAL DEVICE

(71) Applicant: TERUMO KABUSHIKI KAISHA, Tokyo (JP)

(72) Inventor: Yosuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 564 days.

(21) Appl. No.: 17/879,036

(22) Filed: Aug. 2, 2022

(65) Prior Publication Data

US 2022/0370013 A1    Nov. 24, 2022

Related U.S. Application Data

(63) Continuation of application No. PCT/JP2021/007348, filed on Feb. 26, 2021.

(30) Foreign Application Priority Data

Mar. 5, 2020  (JP) .................... 2020-038152

(51) Int. Cl.
| | | |
|---|---|---|
| *A61B 5/00* | (2006.01) | |
| *A61B 5/15* | (2006.01) | |
| *B01D 63/02* | (2006.01) | |
| *G01N 33/49* | (2006.01) | |

(52) U.S. Cl.
CPC ...... *A61B 5/6866* (2013.01); *A61B 5/150221* (2013.01); *A61B 5/150992* (2013.01); *B01D 63/02* (2013.01); *G01N 33/49* (2013.01)

(58) Field of Classification Search
CPC ............ A61B 5/6866; A61B 5/150221; A61B 5/150992; A61B 5/157; A61B 5/15003; A61B 5/155; B01D 63/02; G01N 33/49; G01N 1/00; A61M 1/14; A61M 1/36
See application file for complete search history.

(56) References Cited

U.S. PATENT DOCUMENTS

| | | | |
|---|---|---|---|
| 5,302,348 A | 4/1994 | Cusack et al. | |
| 2014/0112828 A1* | 4/2014 | Grant ................. | A61M 1/1686 210/232 |
| 2014/0262983 A1* | 9/2014 | Tuckwell .......... | A61M 1/36222 73/861.11 |

(Continued)

FOREIGN PATENT DOCUMENTS

| | | |
|---|---|---|
| JP | 2000000299 A1 | 1/2000 |
| JP | 2011045450 A1 | 3/2011 |

OTHER PUBLICATIONS

International Search Report, PCT/JP2021/007348, Mar. 23, 2021.
International Preliminary Opinion, PCT/JP2021/007348, Apr. 6, 2021.

*Primary Examiner* — May A Abouelela
(74) *Attorney, Agent, or Firm* — MacMillan, Sobanski & Todd, LLC

(57) ABSTRACT

A medical device is configured to be attached to a part of a circulation circuit of an extracorporeal circulation device and to be inserted with an insertion member for performing a test related to blood clotting, and includes a storage portion configured to store a blood, and a main body portion configured to drop the blood stored in the storage portion onto the insertion member. The stored blood is used as samples for testing and monitoring of blood conditions (e.g., clotting) during extracorporeal circulation.

10 Claims, 4 Drawing Sheets

(56) References Cited

U.S. PATENT DOCUMENTS

| | | | |
|---|---|---|---|
| 2014/0272920 A1* | 9/2014 | Potenziano | A61M 1/3623 435/1.1 |
| 2014/0276376 A1* | 9/2014 | Rohde | A61M 1/1605 604/29 |
| 2014/0299544 A1* | 10/2014 | Wilt | A61M 1/154 417/474 |
| 2016/0270733 A1* | 9/2016 | Hansson | A61M 1/3639 |
| 2017/0000940 A1* | 1/2017 | Schultz | A61M 1/3622 |
| 2017/0189596 A1* | 7/2017 | Lauer | A61M 1/362262 |
| 2017/0319767 A1* | 11/2017 | Zaniboni | B01D 63/02 |
| 2018/0055988 A1* | 3/2018 | Brun | A61M 1/3672 |
| 2018/0110913 A1* | 4/2018 | Loderer | G01F 1/74 |
| 2019/0070352 A1* | 3/2019 | Tsubouchi | A61B 5/1473 |
| 2019/0151528 A1* | 5/2019 | Li | A61M 1/36 |
| 2019/0358388 A1* | 11/2019 | Yuds | A61M 1/3672 |
| 2021/0278361 A1* | 9/2021 | Yoshimi | C08F 292/00 |
| 2022/0042067 A1* | 2/2022 | Matsuoka | G01N 33/5308 |

\* cited by examiner

MEDICAL DEVICE

CROSS REFERENCE TO RELATED APPLICATIONS

This application is a continuation of PCT Application No. PCT/JP2021/007348, filed Feb. 26, 2021, based on and claiming priority to Japanese Application No. JP2020-038152, filed Mar. 5, 2020, both of which are incorporated herein by reference in their entirety.

BACKGROUND OF THE INVENTION

The present invention relates to a medical device.

In the related art, a treatment with a percutaneous cardiopulmonary support (PCPS) is performed in order to perform cardiopulmonary resuscitation, circulation support, and respiration support in an emergency treatment. The percutaneous cardiopulmonary support is a method of temporarily supplementing or replacing a cardiopulmonary function by using an extracorporeal circulation device.

Since the blood flowing through a circulation circuit of the extracorporeal circulation device is in an environment in contact with a foreign substance such as an oxygenator or a tube, there is a possibility that the blood clots due to activation and forms a thrombus. Therefore, it is necessary for an operator to prevent the thrombus from being formed by administering an anticlotting agent such as heparin into the blood during a treatment.

Meanwhile, when the anticlotting agent is excessively administered at a time, there is a possibility of causing irregular bleeding, cerebral hemorrhage, and the like. Therefore, it is desirable that the operator perform a blood clotting test for testing coagulability of the blood during the treatment, and adjust a dosage of the anticlotting agent on the basis of the test result.

Examples of a method of the blood clotting test include a method of measuring an activated clotting time (ACT), and the method is relatively simple and acquires a test result in a short time. According to the method of measuring an activated clotting time, the clotting time of the blood activated by adding a clotting promoter can be measured to obtain an index of coagulability of the blood.

For example, U.S. Pat. No. 5,302,348 below discloses a method in which a clotting promoter is added to a blood contained in a thin tubular test tube (test container), the blood is caused to flow in the test tube, and flow characteristics thereof are observed to measure an activated clotting time.

However, since the activated clotting time of the blood changes from moment to moment, the operator needs to measure the activated clotting time over a plurality of times during a treatment, and the operator is required to have a skill of sampling a predetermined amount of blood many times. In addition, for example, the operator samples the blood by collecting the blood from a three-way stopcock disposed in the circulation circuit and transferring the blood to the test container. However, when the operator frequently opens the three-way stopcock, there is a possibility that various bacteria and the like in the atmosphere come into contact with the blood flowing through the circulation circuit through an opening of the three-way stopcock. Therefore, it may be difficult for the operator to accurately sample a predetermined amount of the blood while preventing the blood flowing through the circulation circuit of the extracorporeal circulation device from being contaminated by various bacteria and the like.

SUMMARY OF THE INVENTION

The present invention has been made in view of the above circumstances, and an object of the present invention is to provide a medical device capable of collecting a predetermined amount of blood.

A medical device for achieving the above object is a medical device configured to be attached to a part of a circulation circuit of an extracorporeal circulation device and be inserted with an insertion member for performing a test related to blood clotting, and includes a storage portion configured to store a blood, and a main body portion configured to redirect the blood stored in the storage portion onto the insertion member. More specifically, the invention may comprise a medical device configured to be attached to a part of a circulation circuit of an extracorporeal circulation device and be inserted with an insertion member to extract a sample of blood from the circulation circuit for performing a test related to blood clotting. The medical device may comprise a housing with a guide portion (for selectably inserting and removing the insertion member), a storage portion (to store the sample of blood), and a main body portion. The storage portion has a blood-inlet communication hole configured to receive the sample of blood from the part of the circulation circuit and a blood-outlet communication hole. The main body portion is configured to divert the blood stored in the storage portion onto the insertion member, wherein the main body portion has a discharge port in communication with the storage portion which is configured to align with a blood-receiving hole of the insertion member when the insertion member is inserted.

According to the medical device configured as described above, the blood collected from the blood flowing through the circulation circuit of the extracorporeal circulation device is stored, and the stored blood can be redirected (contained) in the insertion member (test container for performing a test related to blood clotting). Therefore, the operator can collect a predetermined amount of the blood in the insertion member.

DETAILED DESCRIPTION OF PREFERRED EMBODIMENTS

Extracorporeal Circulation Device

An extracorporeal circulation device 1 to which a medical device according to an embodiment of the present invention is attached will be described with reference to FIG. 1.

The extracorporeal circulation device 1 can perform a veno-arterial (VA) procedure of removing a blood from a vein (vena cava) of a patient by operating a pump, exchanging gas in the blood with an oxygenator 2 to oxygenate the blood, and then returning the blood to an artery (aorta) of the patient. The extracorporeal circulation device 1 is a device that supports a heart and a lung. Hereinafter, a procedure of removing the blood from a patient, performing a predetermined treatment outside the body, and then supplying the blood into the body of the patient is referred to as "extracorporeal circulation".

Figure 1:
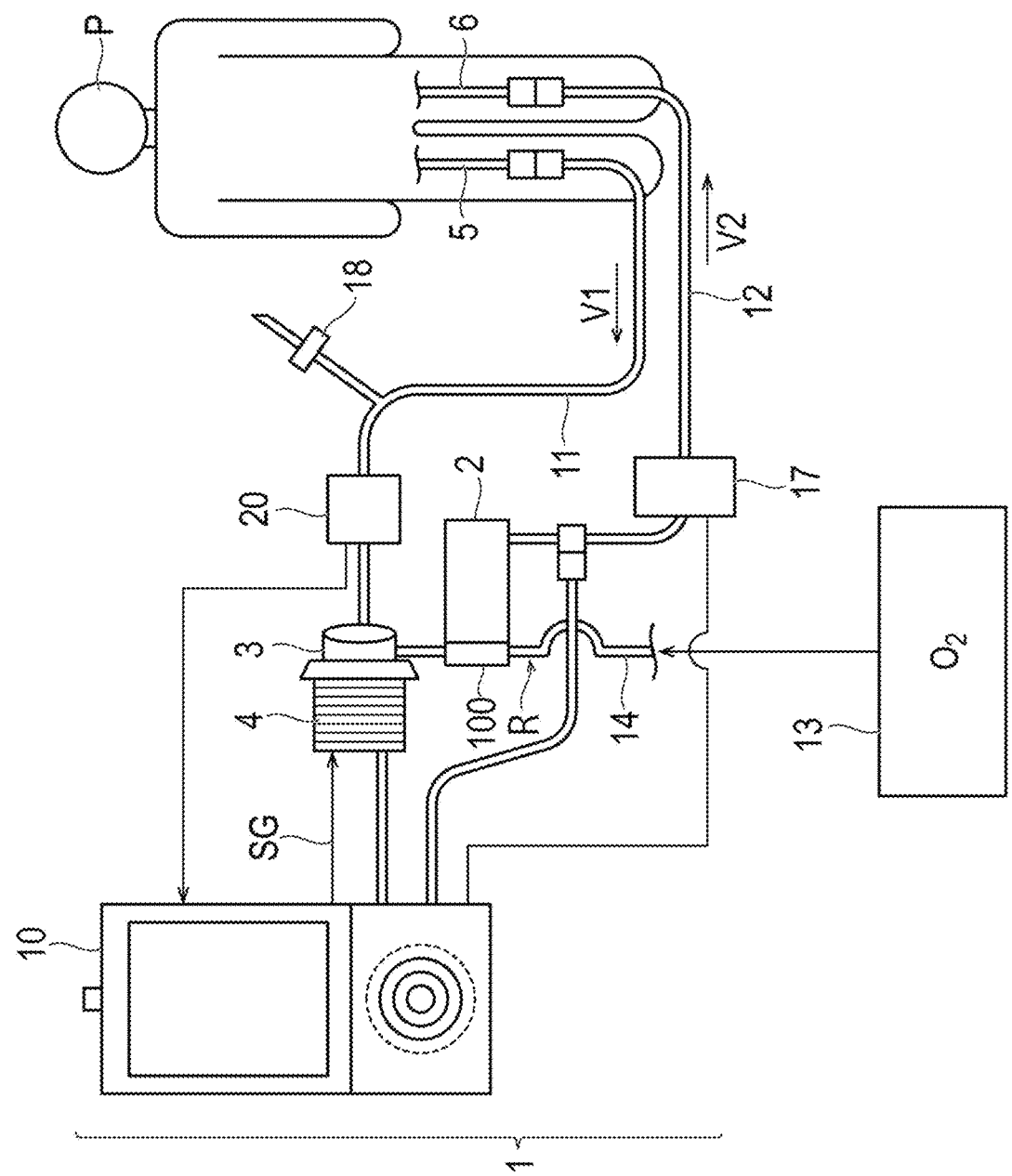
FIG. 1 is a system diagram illustrating an example of an extracorporeal circulation device to which a medical device according to an embodiment of the present invention is attached.

As illustrated in FIG. 1, the extracorporeal circulation device 1 includes a circulation circuit R for circulating the blood. The circulation circuit R includes the oxygenator 2, a centrifugal pump 3, a drive motor 4 which is a drive unit for driving the centrifugal pump 3, a venous side catheter (percutaneous catheter for blood removal) 5, an arterial side catheter (blood supply catheter) 6, and a controller 10 as a control unit.

The venous side catheter (blood removal catheter) 5 is inserted from a femoral vein, and a distal end of the venous side catheter 5 is placed in a right atrium via an inferior vena cava. The venous side catheter 5 is connected to the centrifugal pump 3 through a blood removal tube (blood removal line) 11. The blood removal tube 11 is a conduit for sending the blood.

The arterial side catheter (blood supply catheter) 6 is inserted from a femoral artery.

When the drive motor 4 operates the centrifugal pump 3 according to a command SG from the controller 10, the centrifugal pump 3 can remove the blood from the blood removal tube 11, pass the blood through the oxygenator 2, and then return the blood to a patient P through a blood supply tube (blood supply line) 12.

The oxygenator 2 is disposed between the centrifugal pump 3 and the blood supply tube 12. The oxygenator 2 performs gas exchange (oxygenation and/or carbon dioxide removal) on the blood. The oxygenator 2 is, for example, a membrane oxygenator, and is particularly preferably a hollow fiber membrane oxygenator. Oxygen gas is supplied from an oxygen gas supply unit 13 to the oxygenator 2 through a tube 14. The blood supply tube 12 is a conduit coupling the oxygenator 2 and the arterial side catheter 6.

As the blood removal tube 11 and the blood supply tube 12, for example, a conduit made of a synthetic resin having high transparency and flexibility, i.e., elastically deformable, such as a vinyl chloride resin or a silicone rubber can be used. In the blood removal tube 11, the blood as a liquid flows in a V1 direction, and in the blood supply tube 12, the blood flows in a V2 direction.

In the circulation circuit R illustrated in FIG. 1, an ultrasonic bubble detection sensor 20 is disposed in the middle of the blood removal tube 11. A fast clamp 17 is disposed in the middle of the blood supply tube 12.

When air bubbles are mixed in the circuit due to an erroneous operation on a three-way stopcock 18, breakage of the tube, or the like during the extracorporeal circulation, the ultrasonic bubble detection sensor 20 detects the mixed air bubbles. When the ultrasonic bubble detection sensor 20 detects that the air bubbles are present in the blood sent into the blood removal tube 11, the ultrasonic bubble detection sensor 20 sends a detection signal to the controller 10. Based on the detection signal, the controller 10 notifies a warning by an alarm, and lowers a rotation speed of the centrifugal pump 3, or stops the centrifugal pump 3. Further, the controller 10 commands the fast clamp 17 to immediately close the blood supply tube 12 by the fast clamp 17. Accordingly, the air bubbles are prevented from being sent into the body of the patient P. In this manner, the controller 10 controls an operation of the extracorporeal circulation device 1 to prevent the air bubbles from mixing into the body of the patient P.

Insertion Member

In the present invention, a medical device 100 attached to the circulation circuit R partially collects the blood flowing through the circulation circuit R and redirects the blood onto an insertion member N (i.e., a carrier), so that the blood necessary for a blood clotting test is secured.

Figure 2:
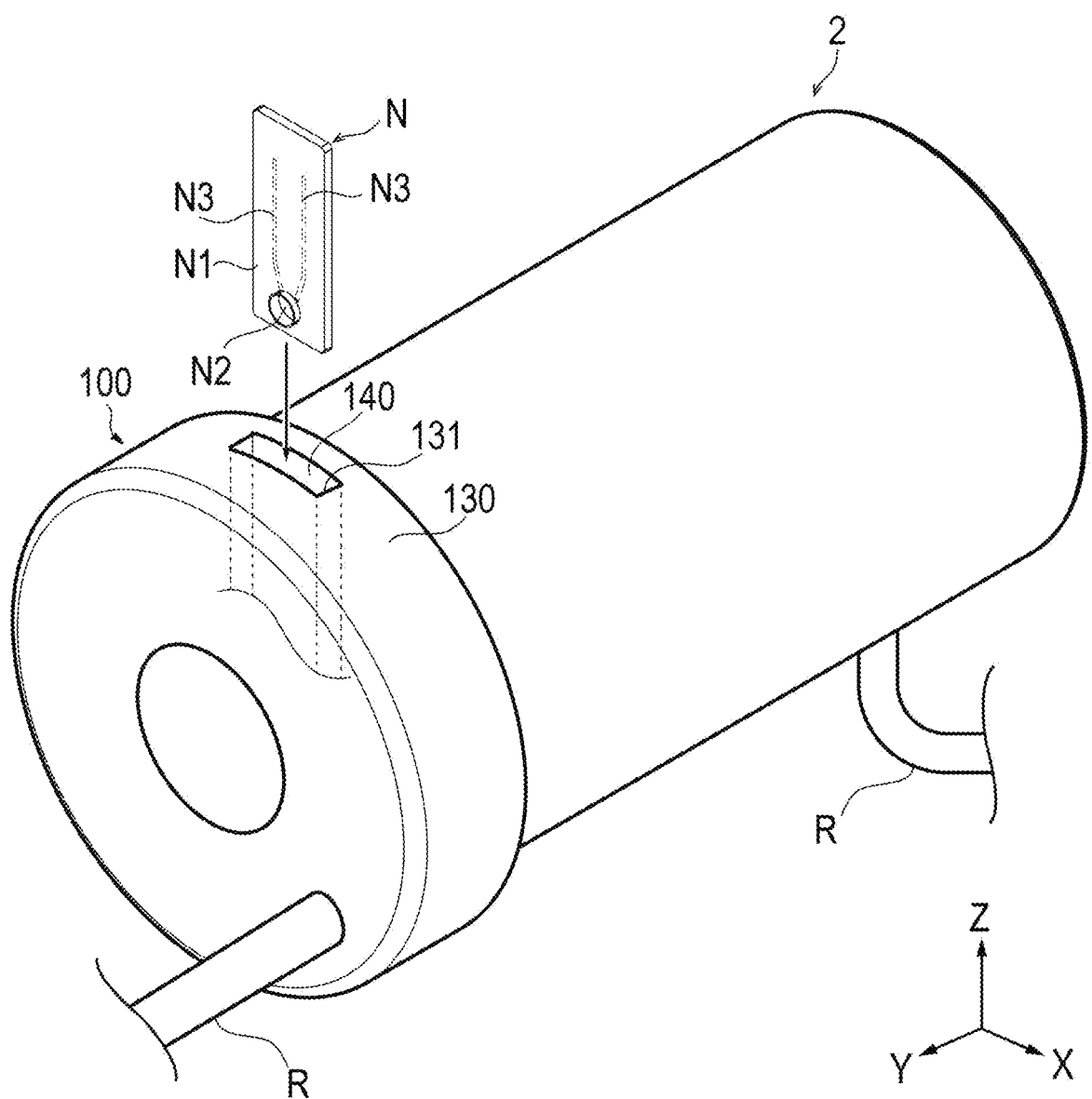
FIG. 2 is a schematic diagram illustrating an oxygenator to which the medical device according to the embodiment of the present invention is attached.

The insertion member N is a cuvette that can be conveyed to and used in a separate device (i.e., analyzer) for performing the blood clotting test. As illustrated in FIG. 2, the insertion member N includes a main body portion N1, an opening N2, and a plurality of conduits N3.

The opening N2 is provided in a surface of the main body portion N1 (a face of an end portion on a minus side in a Z direction in FIG. 2 and on a plus side in a Y direction in FIG. 2). A distal end side of the insertion member N, which is a leading end portion provided with the opening N2, is to be inserted to an inside of the medical device 100 through an insertion port 131. Then, the insertion member N can introduce the blood diverted (e.g., dropped) from a main body portion 120 through the opening N2 and store the blood in the conduits N3 (see FIGS. 3A to 3C).

When the insertion member N is taken out from the medical device 100, the insertion member N is inserted into an analyzer (not illustrated), and the blood clotting test is performed. Then, when the blood clotting test is completed, an activated clotting time of the blood in the insertion member N is displayed on a display panel or the like of the analyzer. In addition, the insertion member N is a disposable test container, and the analyzer can perform a test without coming into contact with the blood contained in the insertion member N. Therefore, when performing the blood clotting test a plurality of times, an operator does not need to clean the analyzer at each test by sterilization or other methods, and can shorten a preparation time for performing the blood clotting test.

First Embodiment

The medical device 100 according to a first embodiment of the present invention will be described with reference to FIG. 2 and FIGS. 3A to 3C.

As illustrated in FIG. 2, the medical device 100 is configured to be attached to the oxygenator 2 provided in the circulation circuit R.

Figure 3A:
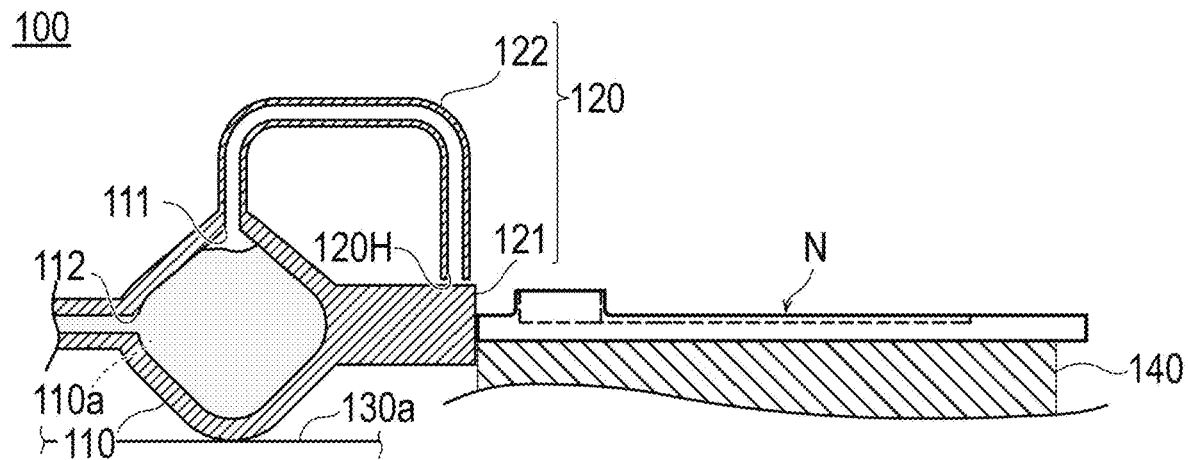
FIG. 3A is a diagram illustrating a function of the medical device according to the present embodiment.

As illustrated in FIGS. 2 and 3A, the medical device 100 includes a storage portion 110 that stores the blood, the main body portion 120 that dispenses (i.e., drops) the blood stored in the storage portion 110 onto the insertion member N, a housing 130 that holds the storage portion 110 and the main body portion 120, and a guide portion 140 on which the insertion member N can be placed and that guides a position of the insertion member N with respect to the main body portion 120.

The housing 130 holds the storage portion 110 and the main body portion 120. The guide portion 140 is provided inside the housing 130 (see FIG. 2).

As illustrated in FIG. 2, the insertion port 131 is provided in an outer periphery of the housing 130. The insertion port 131 is configured to allow the insertion member N to be taken in and out of the medical device 100.

The storage portion 110 is connected to the circulation circuit R. The storage portion 110 can partially collect the blood flowing through the circulation circuit R and store the blood in a storage space 110*a*.

Furthermore, the storage portion 110 is a deformable container made of an elastic material. Examples of a material constituting the storage portion 110 include synthetic resins such as vinyl chloride, various rubber materials such as natural rubber, butyl rubber, isoprene rubber, butadiene rubber, styrene-butadiene rubber, and silicone rubber, various thermoplastic elastomers such as polyurethane-based, polyester-based, polyamide-based, olefin-based, and styrene-based elastomers, or a mixture thereof. Note that the material constituting the storage portion 110 may be a resin material or a metal material as long as this material is an elastically deformable elastic member.

Furthermore, the storage portion 110 includes a blood-outlet communication hole 111 connecting the storage portion 110 to the main body portion 120, and a blood-inlet communication hole 112 connecting the storage portion 110 to the circulation circuit R (see FIG. 3A).

Figure 3B:
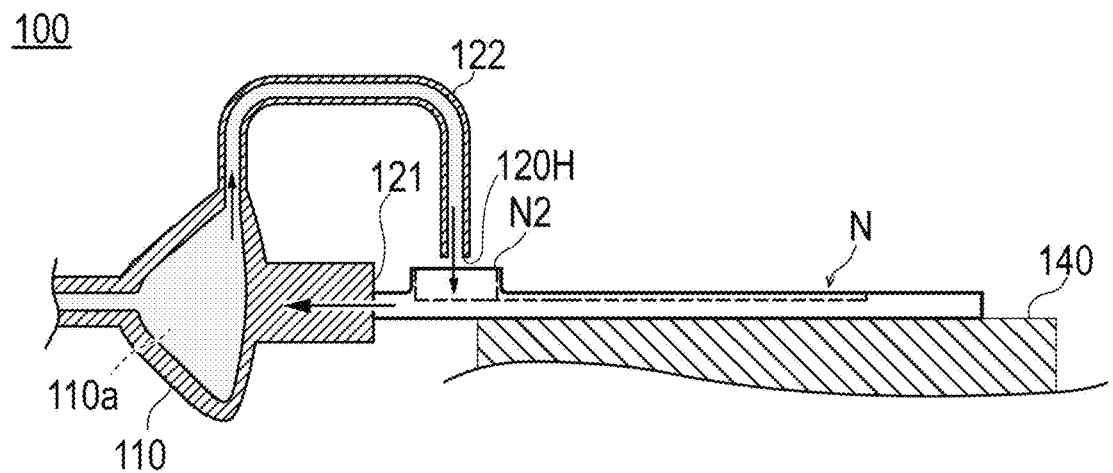
FIG. 3B is a diagram illustrating another function of the medical device according to the present embodiment.
Figure 3C:
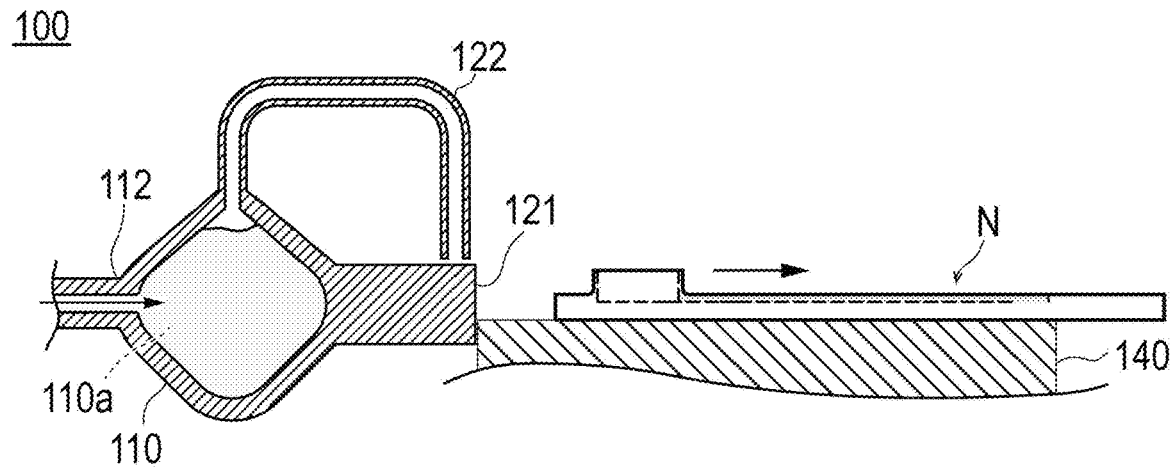
FIG. 3C is a diagram illustrating another function of the medical device according to the present embodiment.

As illustrated in FIGS. 3A to 3C, the main body portion 120 includes a pressing portion 121 configured to deform the storage portion 110 by being pressed by the insertion member N, and a nozzle portion 122 that dispenses the blood sent out from the storage portion 110 by the pressing portion 121 onto the insertion member N.

The pressing portion 121 is formed integrally with the storage portion 110.

One end portion of the nozzle portion 122 is in liquid tight or airtight communication with the storage space 110*a* through the communication hole 111. Furthermore, the other end portion of the nozzle portion 122 includes a discharge port 120H through which the blood stored in the storage portion 110 drops.

According to the medical device 100 of the present embodiment, the insertion member N inserted through the insertion port 131 moves inside the housing 130 along the guide portion 140 until it abuts the pressing portion 121 of the main body portion 120 located on a front side in an insertion direction (see FIG. 3A).

Then after continued movement in the insertion direction, the insertion member N presses the pressing portion 121 (see FIG. 3B). In this case, the opening N2 of the insertion member N is displaced until it is disposed directly below or in the vicinity of the discharge port 120H of the nozzle portion 122.

Additionally, the insertion member N deforms the storage portion 110 by pressing the pressing portion 121. In this case, the storage space 110*a* is deformed in a contracting direction, and the blood stored in the storage space 110*a* is sent out to the nozzle portion 122 through the communication hole 111.

Accordingly, in the medical device 100, the insertion member N presses the pressing portion 121, and the pressed main body portion 120 deforms the storage portion 110, so that the blood stored in the storage portion 110 can be dropped to the opening N2 of the insertion member N through the discharge port 120H of the nozzle portion 122 communicating with the storage portion 110.

A predetermined amount of the blood in opening N2 flows into and is contained by the conduits N3. Then, the insertion member N is taken out (see FIG. 3C) from the medical device 100 through the insertion port 131 (see FIG. 2). The removed insertion member N is then inserted into the analyzer for performing the blood clotting test as described above.

When the insertion member N is taken out from the medical device 100, the storage portion 110 is deformed in a direction where the storage space 110*a* expands (i.e., elastically returns to its original shape shown in FIG. 3C). In this case, since an internal pressure of the storage space 110*a* of the storage portion 110 changes from a positive pressure to a negative pressure, the blood flowing through the circulation circuit R flows into the storage portion 110 again through the communication hole 112.

Accordingly, the medical device 100 can repeatedly perform an operation of collecting a predetermined amount of the blood from the blood flowing through the circulation circuit R and storing the collected blood in the storage portion 110, and an operation of dropping (collecting) the blood stored in the storage portion 110 onto the insertion member N by the main body portion 120.

As described above, the medical device 100 according to the present embodiment is a medical device configured to be attached to a part of the circulation circuit R of the extracorporeal circulation device 1 and to be inserted with the insertion member N for performing a test related to blood clotting, and includes the storage portion 110 that stores the blood, and the main body portion 120 that drops the blood stored in the storage portion 110 onto the insertion member N.

According to the medical device 100 configured as described above, the blood flowing in the circulation circuit R of the extracorporeal circulation device 1 can be collected and stored in the storage portion 110, and the blood stored in the storage portion 110 can be dropped onto the insertion member N (test container for performing a test related to blood clotting) by the main body portion 120. Therefore, the operator can collect a predetermined amount of the blood on the insertion member N.

Furthermore, the main body portion 120 includes the pressing portion 121 configured to deform the storage portion 110 by being pressed by the insertion member N, and the nozzle portion 122 that drops the blood sent out from the storage portion 110 onto the insertion member N by the pressing portion 121. Accordingly, in the medical device 100, the main body portion 120 deforms the storage portion 110, so that the blood stored in the storage portion 110 can be dropped to the opening N2 of the insertion member N from the nozzle portion 122 communicating with the storage portion 110.

Furthermore, the storage portion 110 is formed of an elastic material. Accordingly, the medical device 100 can repeatedly perform the operation of collecting a predetermined amount of the blood from the blood flowing through the circulation circuit R of the extracorporeal circulation device 1 and storing the collected blood in the storage portion 110, and the operation of dropping the blood stored in the storage portion 110 onto the insertion member N by the main body portion 120.

Second Embodiment

Figure 4:
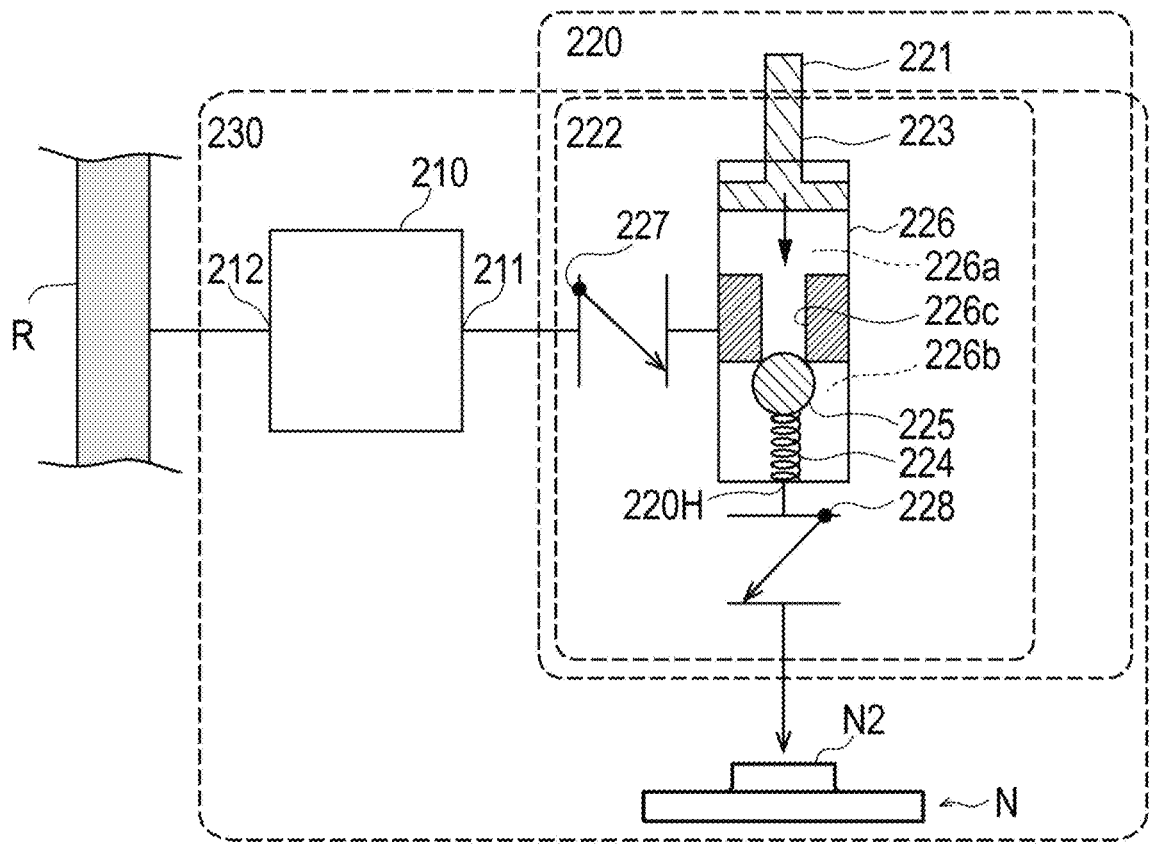
FIG. 4 is a diagram schematically illustrating a medical device according to a second embodiment.

A medical device 200 according to a second embodiment of the present invention will be described with reference to FIG. 4. Note that descriptions of the same configurations as those of the first embodiment will be omitted.

The medical device 200 includes a storage portion 210, a main body portion 220, a housing 230, and a guide portion (not illustrated).

In addition, the main body portion 220 includes a button 221 and a valve portion 222 that drops the blood stored in the storage portion 210 onto the insertion member N when the button 221 is pressed.

The housing 230 holds the storage portion 210, the main body portion 220, and the guide portion (not illustrated).

An insertion port (not illustrated) is provided in an outer periphery of the housing 230.

The storage portion 210 is a non-deformable container. A communication hole 211 connected to the valve portion 222 and a communication hole 212 connected to the circulation circuit R are formed in the storage portion 210.

The button 221 refers to a portion of a plunger 223 protruding from the housing 230, and is configured to be pressed by the operator.

The valve portion 222 is a spring return valve. The valve portion 222 includes the plunger 223, a spring 224, a plug 225, a cylinder 226, and a plurality of check valves 227 and 228.

When the button 221 is pressed by the operator, the plunger 223 can push out the blood contained in the cylinder 226 from a supply port side of the cylinder 226 to a discharge port 220H side.

The cylinder 226 includes a first cylinder chamber 226a provided on the supply port side and a second cylinder chamber 226b provided on the discharge port 220H side.

A connection port 226c between the first cylinder chamber 226a and the second cylinder chamber 226b is configured to be opened and closed by the plug 225 disposed on a second cylinder chamber 226b side. The plug 225 is provided on the other end side of the spring 224 having one end side connected to the second cylinder chamber 226b side, and is pressed against the connection port 226c (blocks the connection port 226c) or moved away from the connection port 226c (opens the connection port 226c) by a biasing force of the spring 224.

The check valve 227 prevents backflow of the blood from the first cylinder chamber 226a into the storage portion 210. Furthermore, the check valve 228 prevents backflow of the blood from the discharge port 220H of the valve portion 222 into the second cylinder chamber 226b.

According to the medical device 200 of the second embodiment, the insertion member N inserted from the insertion port (not illustrated) moves inside the housing 230 along the guide portion (not illustrated). Then, the opening N2 of the insertion member N is disposed directly below or in the vicinity of the discharge port 220H of the valve portion 222.

Then, when the button 221 is pressed by the operator, the blood stored in the storage portion 210 flows into the first cylinder chamber 226a of the valve portion 222. Then, the plunger 223 moves toward a connection port 226c side so as to reduce a volume of the first cylinder chamber 226a. Accordingly, the blood contained in the first cylinder chamber 226a applies an external force to the plug 225 blocking the connection port 226c in a direction where the spring 224 contracts. Accordingly, the plug 225 moves in a direction where the connection port 226c is opened. Therefore, the blood stored in the first cylinder chamber 226a flows into the second cylinder chamber 226b.

Accordingly, in the medical device 200, the operator presses the button 221 to operate the plunger 223 connected to the button 221, so that the blood stored in the storage portion 210 can be dropped to the opening N2 of the insertion member N through the discharge port 220H of the valve portion 222 communicating with the storage portion 210.

Then, when the insertion member N is taken out from the medical device 200, the spring 224 expands to press the plug 225 against the connection port 226c. Therefore, the connection port 226c is blocked by the plug 225. Then, the blood flowing through the circulation circuit R flows into the storage portion 210 again through the communication hole 212.

Accordingly, the medical device 200 can repeatedly perform an operation of collecting a predetermined amount of the blood from the blood flowing through the circulation circuit R and storing the collected blood in the storage portion 210, and an operation of dropping the blood stored in the storage portion 210 onto the insertion member N by the main body portion 220.

As described above, the medical device 200 according to the second embodiment is a medical device configured to be attached to a part of the circulation circuit R of the extracorporeal circulation device 1 and to be inserted with the insertion member N for performing a test related to blood clotting, and includes the storage portion 210 that stores the blood, and the main body portion 220 that drops the blood stored in the storage portion 210 onto the insertion member N. Furthermore, the main body portion 220 includes the button 221 configured to be pressed by the operator (user), and the valve portion 222 that drops the blood onto the insertion member N when the button 221 is pressed.

According to the medical device 200 configured as described above, the blood flowing in the circulation circuit R of the extracorporeal circulation device 1 can be collected and stored in the storage portion 210, and the blood stored in the storage portion 210 can be dropped onto the insertion member N (test container for performing a test related to blood clotting) by operating the valve portion 222 linked to the button 221.

Furthermore, the valve portion 222 is a spring return valve. The valve portion 222 can move the plug 225, which controls the flow of the blood in the cylinder 226, by the biasing force of the spring 224.

Although the medical device has been described through the embodiments above, the present invention is not limited to the configurations and the use methods described in the embodiments, and can be appropriately changed based on descriptions of the claims.

Figure 5:
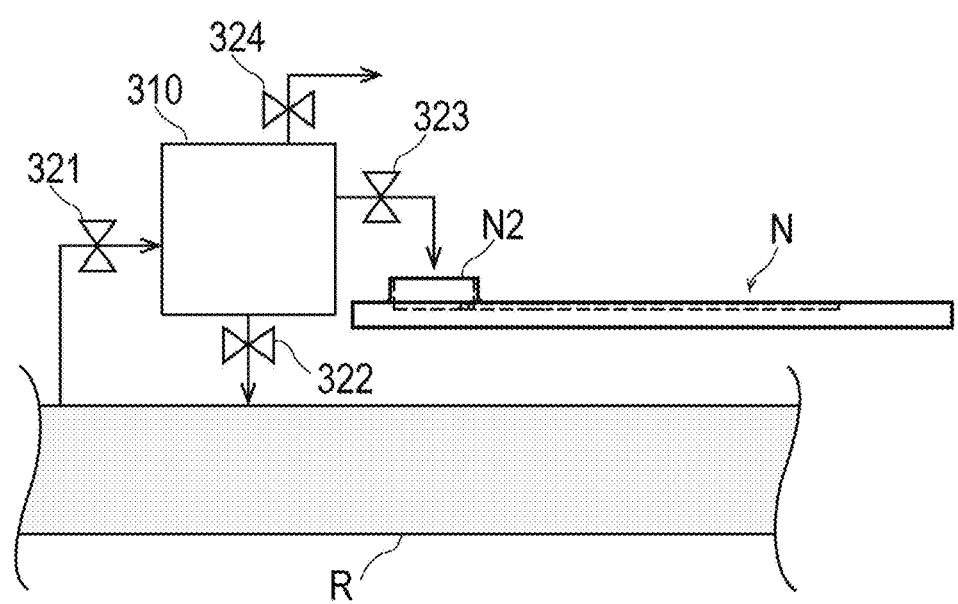
FIG. 5 is a diagram schematically illustrating a medical device according to a modification of the second embodiment.

For example, sampling of the blood by a medical device may be performed by a plurality of valves connected to a storage portion 310. As illustrated in FIG. 5, a medical device 300 may include a suction valve 321, a plurality of discharge valves 322 and 323, and an air valve 324, as a main body portion that drops the blood stored in the storage portion 310 onto the insertion member N.

The suction valve 321 is connected to the circulation circuit R, and can cause the blood flowing through the circulation circuit R to partially flow into the storage portion 310. Further, the discharge valve 322 is connected to the circulation circuit R, and can periodically return the blood stored in the storage portion 310 to the circulation circuit R. Furthermore, the discharge valve 323 can drop the blood stored in the storage portion 310 onto the insertion member N. In addition, the air valve 324 can control an internal pressure of the storage portion 310. According to such a medical device 300, the blood flowing through the circulation circuit R moves back and forth between the circulation circuit R and the storage portion 310. Then, when the insertion member N is inserted into the medical device 300, the medical device 300 can drop the blood stored in the storage portion 310 onto the insertion member N through the discharge valve 323.

What is claimed is:

1. A medical device configured to be attached to a part of a circulation circuit of an extracorporeal circulation device and be inserted with an insertion member to extract a sample of blood from the circulation circuit for performing a test related to blood clotting, the medical device comprising:
    a housing with a guide portion for selectably inserting and removing the insertion member;
    a storage portion configured to store the sample of blood, wherein the storage portion has a blood-inlet communication hole configured to receive the sample of blood from the part of the circulation circuit, and wherein the storage portion has a blood-outlet communication hole; and
    a main body portion configured to divert the blood stored in the storage portion onto the insertion member, wherein the main body portion has a discharge port in communication with the storage portion which is configured to align with a blood-receiving hole of the insertion member when the insertion member is inserted.

2. The medical device according to claim 1, wherein the main body portion is comprised of:
    a pressing portion configured to deform the storage portion by being pressed by the insertion member; and
    a nozzle portion extending from the storage portion to the discharge port and configured to drop the blood sent out from the storage portion onto the insertion member in response to the storage portion being deformed by the pressing portion.

3. The medical device according to claim 2, wherein the storage portion is comprised of an elastic material.

4. The medical device according to claim 1, wherein the main body portion is comprised of:
    a button configured to be pressed by a user; and
    a valve portion configured to drop the blood onto the insertion member when the button is pressed.

5. The medical device according to claim 4, wherein the valve portion is comprised of a spring return valve.

6. A method for sampling blood in an extracorporeal circulation circuit comprising the steps of:
    coupling a medical device to a part of the extracorporeal circulation circuit, wherein the medical device includes (i) a housing with a guide portion for selectably inserting and removing an insertion member which includes a blood-receiving hole in communication with blood-receiving conduits, (ii) a storage portion configured to store a sample of blood wherein the storage portion has a blood-inlet communication hole and a blood-outlet communication hole, and (iii) a main body portion;
    receiving the sample of blood into the storage portion via the blood-inlet communication hole;
    inserting the insertion member into the guide portion;
    extracting the sample of blood by diverting the blood stored in the storage portion to the blood-receiving hole and blood-receiving conduits of the insertion member via a discharge port of the main body when the discharge port is aligned with the blood-receiving hole of the insertion member; and
    removing the insertion member with the sample of blood stored in the blood-receiving conduits for transfer to a separate testing device.

7. The method of claim 6 wherein storage portion is comprised of an elastic material, wherein the main body portion is comprised of a pressing portion configured to deform the storage portion by being pressed by the insertion member, and wherein the main body portion is comprised of a nozzle portion extending from the storage portion to the discharge port which is configured to drop the blood sent out from the storage portion onto the insertion member in response to the storage portion being deformed by the pressing portion.

8. The method of claim 7 wherein the discharge port is configured to align with the blood-receiving hole of the insertion member when the insertion member is inserted to deform the storage portion.

9. The method of claim 6 wherein the main body portion is comprised of a button configured to be pressed by a user and a valve portion configured to drop the blood onto the insertion member when the button is pressed.

10. The method of claim 6 wherein the valve portion is comprised of a spring return valve.

* * * * *